United States Patent [19]

Reynolds

[11] Patent Number: 5,893,373

[45] Date of Patent: Apr. 13, 1999

[54] METHOD FOR APPLICATION OF COSMETICS

[76] Inventor: Justine Bedell Reynolds, Box 442 R.R. 1, Chester, N.J. 07930

[*] Notice: This patent is subject to a terminal disclaimer.

[21] Appl. No.: 08/613,749

[22] Filed: Feb. 23, 1996

Related U.S. Application Data

[63] Continuation-in-part of application No. 08/276,406, Jul. 18, 1994, Pat. No. 5,494,056.

[51] Int. Cl.$^6$ .................................................. A45D 24/00
[52] U.S. Cl. ................................. 132/200; 434/100
[58] Field of Search ............................. 132/200, 293, 132/320; 434/81, 99, 100

[56] References Cited

U.S. PATENT DOCUMENTS

| | | | |
|---|---|---|---|
| 4,957,124 | 9/1990 | Mooney | 132/200 |
| 5,229,121 | 7/1993 | Razzano et al. | 132/200 |
| 5,520,203 | 5/1996 | Segerstrom | 132/293 |

OTHER PUBLICATIONS

"make the most of Your Face", Seventeen, pp. 27–28, Nov. 1984.

"First Blush", Seventeen, p. 60, May 1984.
"20 Steps to Beauty", Seventeen, pp. 122–123, Oct. 1981.

Primary Examiner—Todd E. Manahan

[57] ABSTRACT

Foundation is applied to a preselected area of the face that is centered therewithin and encompasses the eyes, nose and mouth thereof, the process for its application comprising the steps of: (a) placing a sizable first dot of foundation at a first position on each side of the nose near the nostrils; (b) stroking upward from the first position to meet the bridge of the nose; (c) blending the foundation of the first dot to cover the entire front and sides of the nose, whereby the nostrils retain enough of the foundation to cover red skin thereabout; (d) placing a sizable dot of the foundation on each side of the nose at a second position, the second position being under the corner of each eye immediately adjacent to the nose; (e) spreading the foundation of the second dot away from the nose while maintaining heaviest coverage at the second position, thereby covering the skin very close to the lower eyelashes; (f) blending the foundation downward; (g) applying more of the foundation in a back and forth motion at a third position, the third position being above and below the mouth including the bottom of the nose; and (h) stroking the foundation from the outer boundary of the preselected area toward the center of the face, thereby blending the foundation into surrounding skin along substantially the entire length of the outer boundary to define the preselected area. Products appointed for make-up use are correlated and their usage is quantified and controlled. The process is readily repeatable and works for women of all ages and abilities.

14 Claims, 13 Drawing Sheets

METHOD FOR APPLICATION OF COSMETICS

CROSS-REFERENCE TO RELATED APPLICATIONS

This Application is a Continuation-in-Part of U.S. application Ser. No. 08/276,406, filed Jul. 18, 1994, now U.S. Pat. No. 5,494,056.

BACKGROUND OF THE INVENTION

1. Field of the Invention

The present invention relates to a the field of cosmetics; and, more particularly to a method for applying make-up and foundation to a preselected, uniquely shaped area of the human face.

2. Description of the Prior Art

In the '60s and early '70s nearly 50% of American women wore little or no cosmetics, in addition to lipstick, primarily because of the uncomfortable feeling produced when foundation covered the entire face and the difficulty of controlling color during application. As women began to enter the work force at increased levels of professionalism they felt the need to follow the lead of their female peers. Even so, cosmetic sales figures did not rise, but declined instead. Wall Street analysts, mindful of the poor performance of cosmetic industry stocks during the early 1980's concluded that with increasing business exposure professional women had less time to experiment with cosmetics, and had begun to purchase only those cosmetic products they needed to use. Thus, for many women who had previously enjoyed wearing a wider variety of cosmetics, the "guaranteed users," the purchase rate had dropped. Women who had never liked make-up to begin with approached it in a practical manner. Those women who preferred to stay at home raising their families were strongly influenced by cultural changes affecting use of make-up products by their professional counterparts, and the fact that application of make-up continued to be a difficult and time consuming process.

Despite the plethora of secret ingredients and formulas utilized in cosmetic products, there is very little, if any, information available concerning a systematic approach to make-up application. No guidance is provided for clarifying or simplifying make-up usage; and no system has been proposed wherein make-up application is controlled through correlation and quantification of make-up products. Although use of cosmetics is age-old, having begun sometime before the reign of Cleopatra, there still exists no unified, comprehensive approach to make-up application. As a result, application of make-up remains a mystery. It is viewed by the consumer as an art form involving an undefined aggregation of time consuming, inefficient measures that are devoid of scientific underpinnings. An art form involving measures which are not readily repeated and which are generally inapplicable to women of any age or ability.

SUMMARY OF THE INVENTION

The present invention provides a method for applying foundation to a preselected area of the face that is centered within and encompasses the eyes, nose and mouth thereof, comprising the steps of: (a) placing a sizable first dot of foundation at a first position on each side of the nose near the nostrils; (b) stroking upward from said first position to meet the bridge of said nose; (c) blending the foundation of the first dot to cover the entire front and sides of the nose, whereby the nostrils retain enough of the foundation to cover red skin thereabout; (d) placing a dot of the foundation on each side of the nose at a second position, the second position being under the corner of each eye immediately adjacent to the nose; (e) spreading the foundation of the second dot away from the nose while maintaining heaviest coverage at the second position, thereby covering the skin very close to the lower eyelashes; (f) blending the foundation downward; (g) applying more of the foundation in a back and forth motion at a third position, the third position being above and below the mouth including the bottom of the nose; and (h) stroking the foundation from the outer boundary of the preselected area toward the center of the face, thereby blending the foundation into surrounding skin along substantially the entire length of the outer boundary to define the preselected area.

Optionally, the method further comprises the steps of: (l) placing the foundation at a fourth position, the fourth position being between the eyes; (m) blending the foundation upward between the eyes to not more than ½ inch above the brows; and (n) blending at the bridge of the nose into the foundation near the first position, whereby coverage of the foundation is light. As yet another option, the method further comprises the steps of (o) placing the foundation at a fifth position, the fifth position being located in the center of the eyelids; and (p) blending out and up, and into the corner of the eye near the nose.

The present invention provides a comprehensive, unified method for application of make-up. Products appointed for make-up use are correlated and their usage is quantified and controlled. The application of make-up is clarified and simplified. Its existence as an art form is superseded by a process that is scientifically controlled. The process is readily repeatable and works for women of all ages and abilities. It is virtually mistake-proof, speeds up the application procedure and improves the results achieved by novice and professional alike. Use of make-up, and hence cosmetic sales, will increase as customers gain confidence in their ability to initiate and re-do the make-up application process on their own.

BRIEF DESCRIPTION OF THE DRAWINGS

The invention will be more fully understood and further advantages will become apparent when reference is made to the following detailed description of the preferred embodiment of the invention and the accompanying drawings, in which.

DESCRIPTION OF PREFERRED EMBODIMENTS

Figure 1:
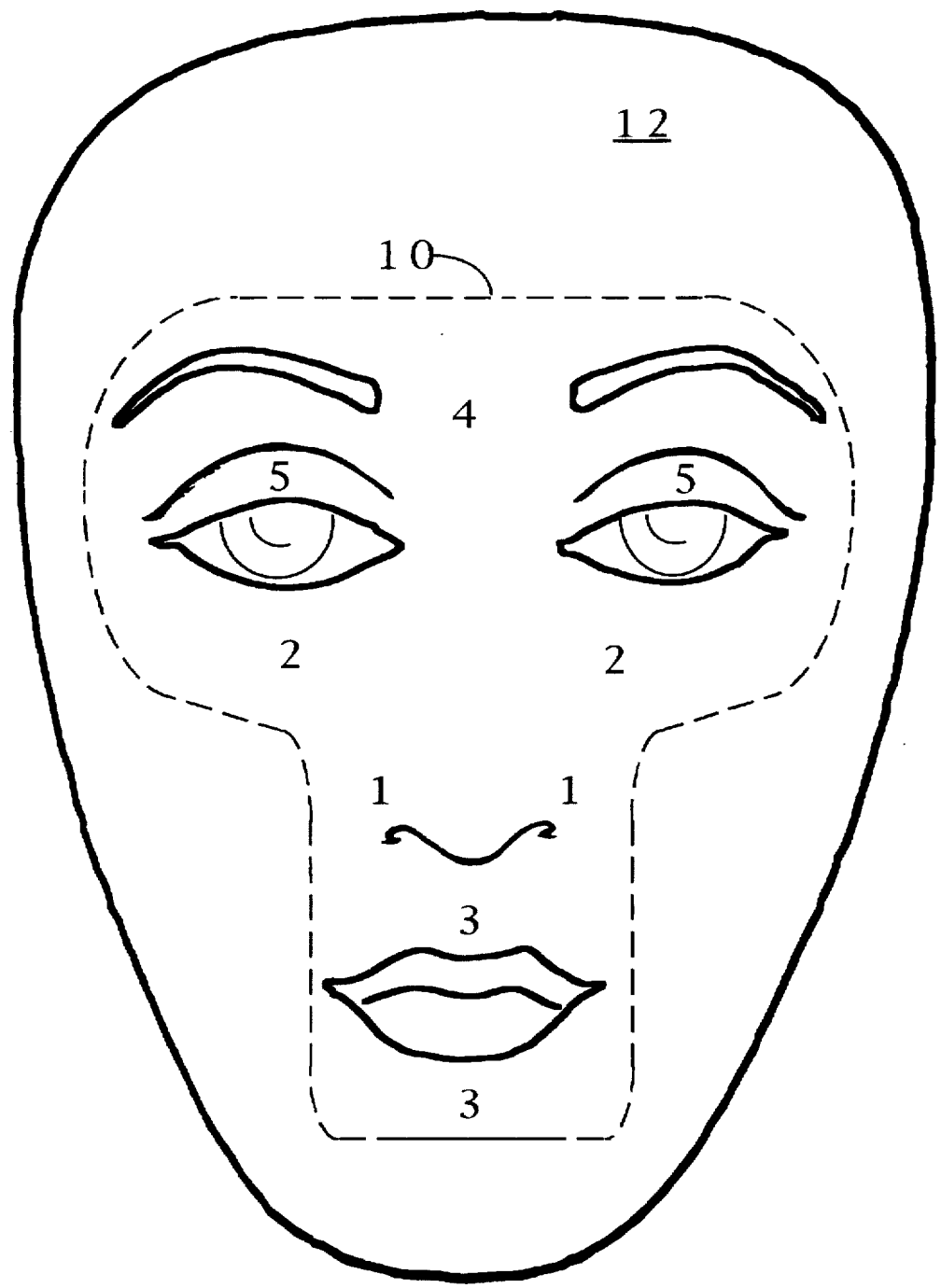
FIG. 1 is a schematic view of a human face bearing a preselected, uniquely shaped area.

Referring to FIG. 1 of the drawings, there is shown, schematically, a human face having a preselected area 10 that is central within and encompasses the eyes, nose and mouth thereof. Foundation is applied to the preselected area 10 at a first position 1, a second position 2, and a third position 3 to control reflection of light from the preselected area 10 and accent or cover certain portions therewithin. In the embodiment shown, the preselected area 10 has a keyhole shape, which shape is preferred for the cosmetic application process of the present invention. Optionally, cosmetics are additionally applied to fourth positions 4, and fifth position 5 within the preselected, keyhole shaped area.

As used herein, the term "cosmetics" includes make-up, foundation, and skin care products. The term "make-up" refers to products that leave color on the face, including foundation, blacks and browns, i.e., mascara, eye liners, brow colors, eye shadows, blushers, lip colors, and so forth. Skin care products are those used to care for, or somehow moisturize, improve, or clean the skin. The term "foundation" refers to liquid, creme, mousse, pancake or like product created or reintroduced by cosmetic companies to even out the overall coloring of the skin. Foundation is manufactured to work better over moisturized and/or oiled skin.

In preparation for the cosmetic application process, the face should be cleaned and then moisturized. Skin which is very oily requires additional cleaning and use of oil-free moisturizers. With all skin types a small amount of oil should be placed under the eyes because of the lack of oil glands there. Cosmetic companies produce eye creams for this purpose. Foundation glides over oiled or moisturized surfaces, preventing a dry look.

Figure 2:
FIG. 2 is a schematic view of a portion of the face showing the first position of foundation application.

Referring to FIG. 2, the process is initiated by placing foundation on the finger of choice. With that finger, the user places a sizable dot of foundation at first position 1 on each side of the nostrils. Then employing what's left on the finger, the user strokes upward from the first position 1 to meet the bridge of the nose and blend the foundation to cover the entire front and sides of the nose. Care should be exercised to ensure that the nostrils retain enough foundation to cover any red colored skin around them. Enlarged pores around the sides of the nostrils should be filled with foundation. It may be necessary to fill such pores with moisturizer before application of foundation. For the best effect, the user should "set" the amount of foundation with loose powder using a big fluffy powder brush. This procedure provides a nice finish; but use of power is optional.

Figure 3:
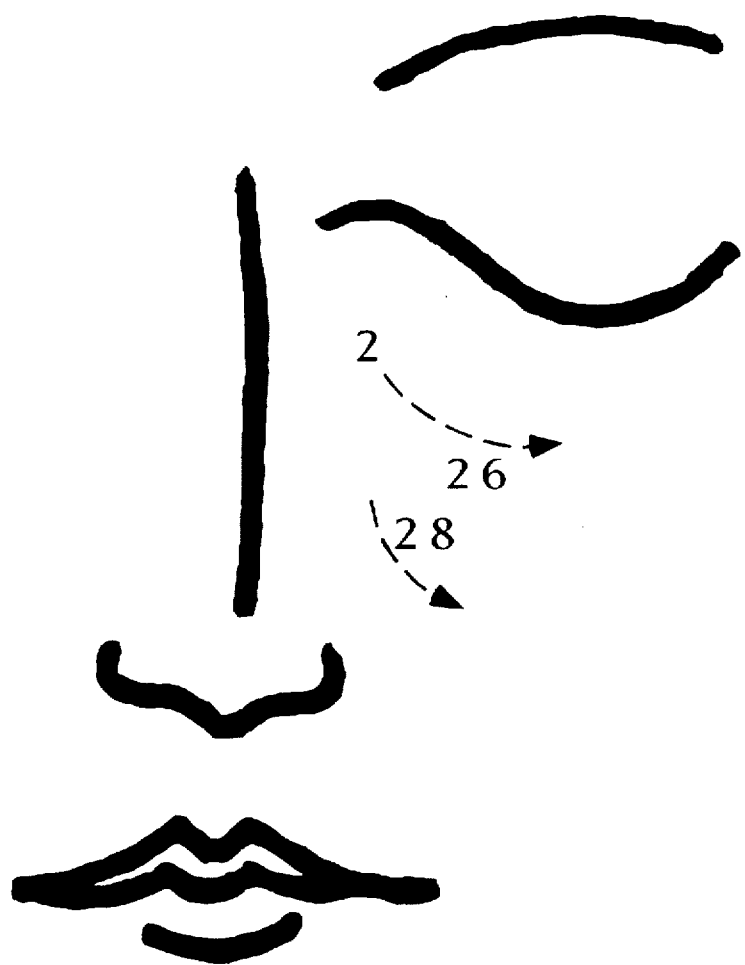
FIG. 3 is a schematic view of a portion of the face showing the second position of foundation application.
Figure 3A:
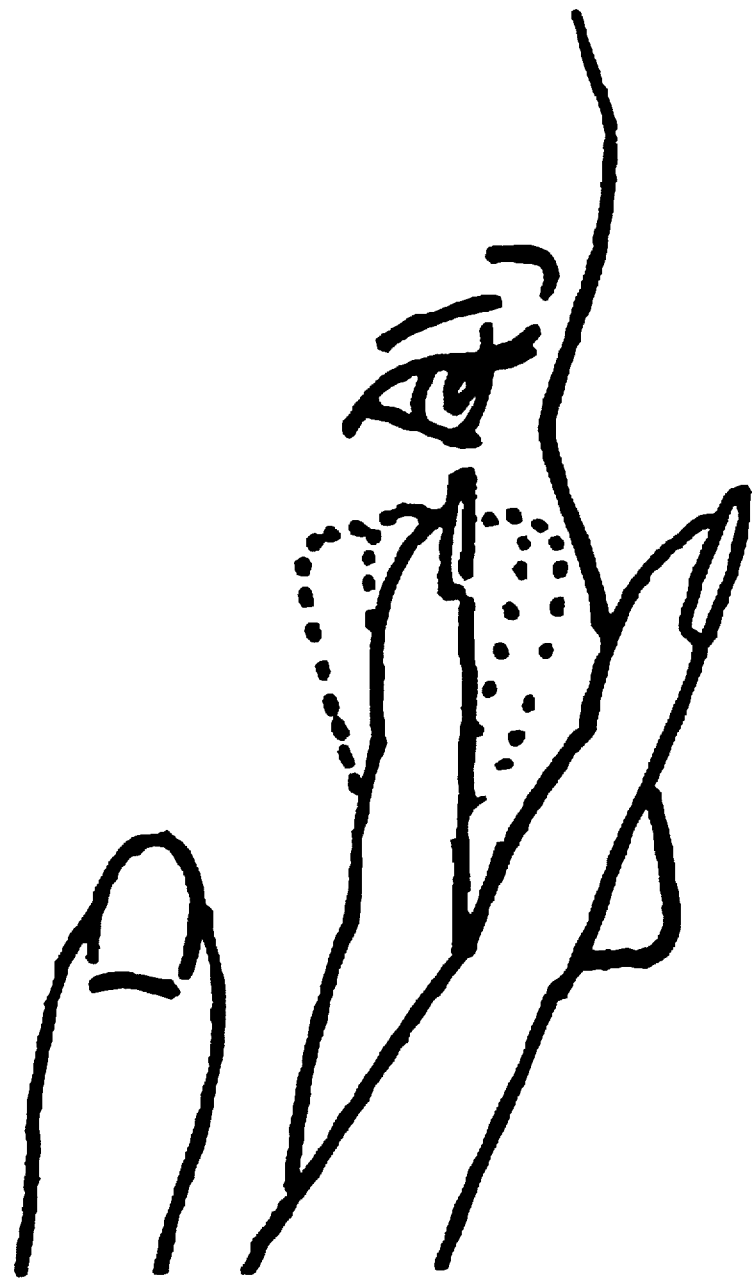
FIG. 3a is a schematic view of application of foundation by patting.

Referring to FIG. 3, the user next puts a small quantum of foundation on the finger and places a dot of foundation at the little deep dark spot under the corner of each eye immediately adjacent to the nose, shown in FIG. 3 as second position 2. This dot of foundation is then spread in the direction of the arrows 26 and 28. During spreading, the skin is covered with foundation along a continuum of points very close to the lower eyelashes, and the foundation is blended downward to the sides of the nose. Enough foundation should be left after spreading to cover substantially the entire dark area under the corner of the eye at second position 2. When covering circles with a foundation alone, a stroking motion is allowable When covering a concealer with foundation, a patting motion must be used. Whenever covering one product with another, a stroking motion will blend the two together, causing a new unintended color. Patting is achieved when using an even, swinging in and out touch and immediate release movement with the finger of choice, as shown in FIG. 3a.

Figure 3B:
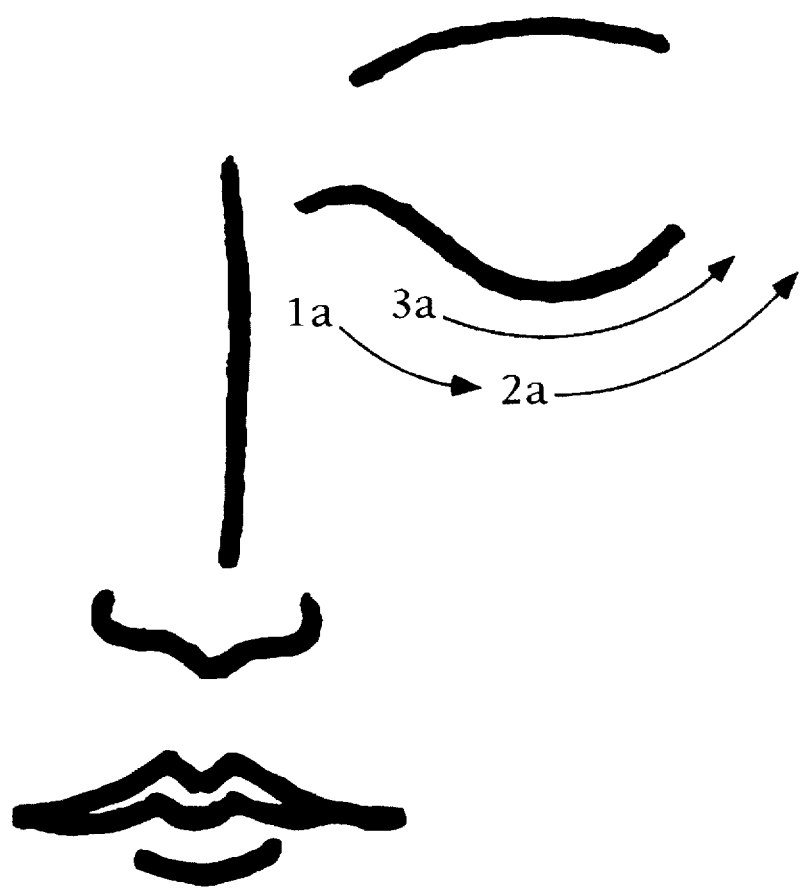
FIG. 3b is a schematic view of a portion of the face showing the positions of application of foundation below the eye.

Referring to FIG. 3b, a concealer is optionally used before applying foundation. With a finger tip place a dot of concealer at first position 1a. Stroke to second position 2a. Next, starting at a third position 3a, directly under the lashes, stroke concealer away from the nose. Patting is used instead of stroking to apply foundation over concealer as described below so as to not create a new unintended color. Foundation is applied under the eye over the concealer starting at a first position 1a and patted toward a second position 2a. Next, starting at a third position 3a, directly under and into the lashes, pat away from the nose.

Figure 4:
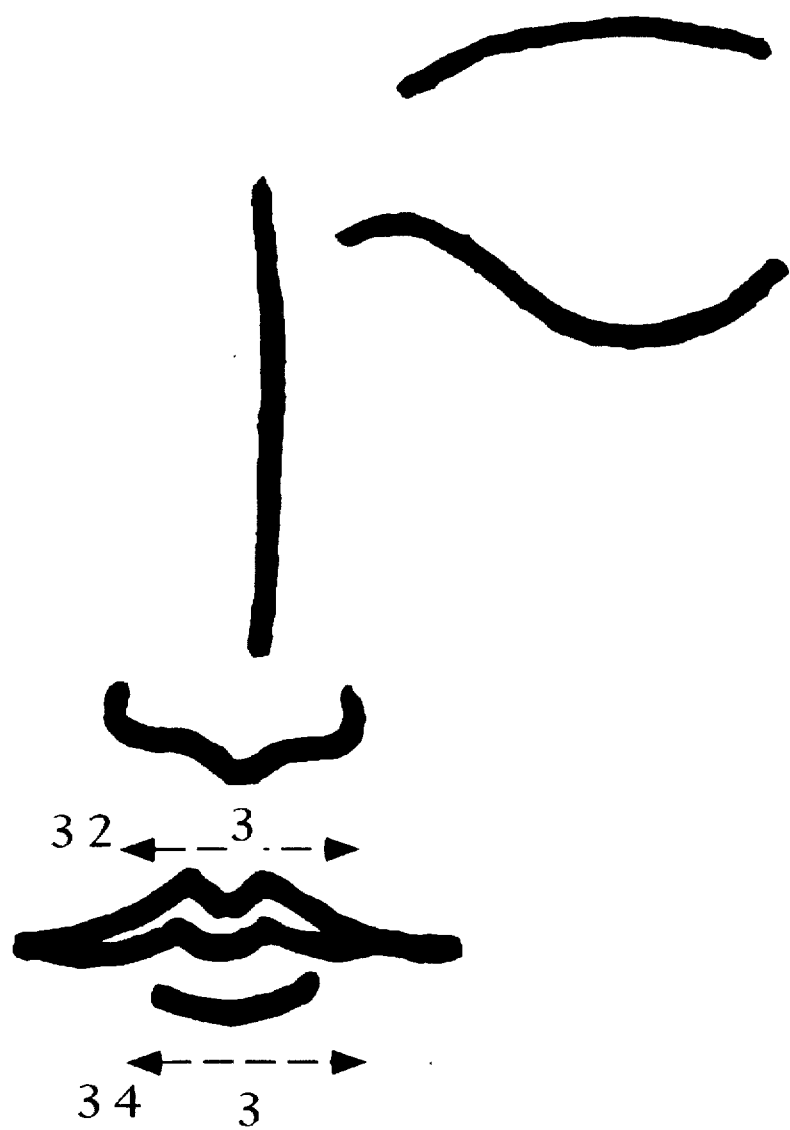
FIG. 4 is a schematic view of a portion of the face showing the third position of foundation application.

Referring to FIG. 4, the user takes more foundation and applies it at third position 3, above and below the mouth. At third position 3, application is accomplished using a back and forth motion, as indicated by the arrows 32 and 34 shown in the FIG. 4. Optionally, an up and down motion can be used over the areas indicated. Care should be taken to apply foundation at the sides of the mouth, restricting such application to a limited amount, to ensure that minimal or no foundation is applied in the smile lines. The quantum of foundation used at the third position 3 should be sufficient to recheck that the bottom of the nostrils become covered just above the mouth.

Optionally, still referring to FIG. 4, if the lips are naturally dark, foundation can be applied to the lips before applying lipstick. If lipstick is not to be used, foundation should be applied to the lips only in the event that the user wishes to diminish their shape or size. In such case application of foundation is restricted to the outer edges of the lips and occurs as described hereinabove along the lip-line.

Figure 5:
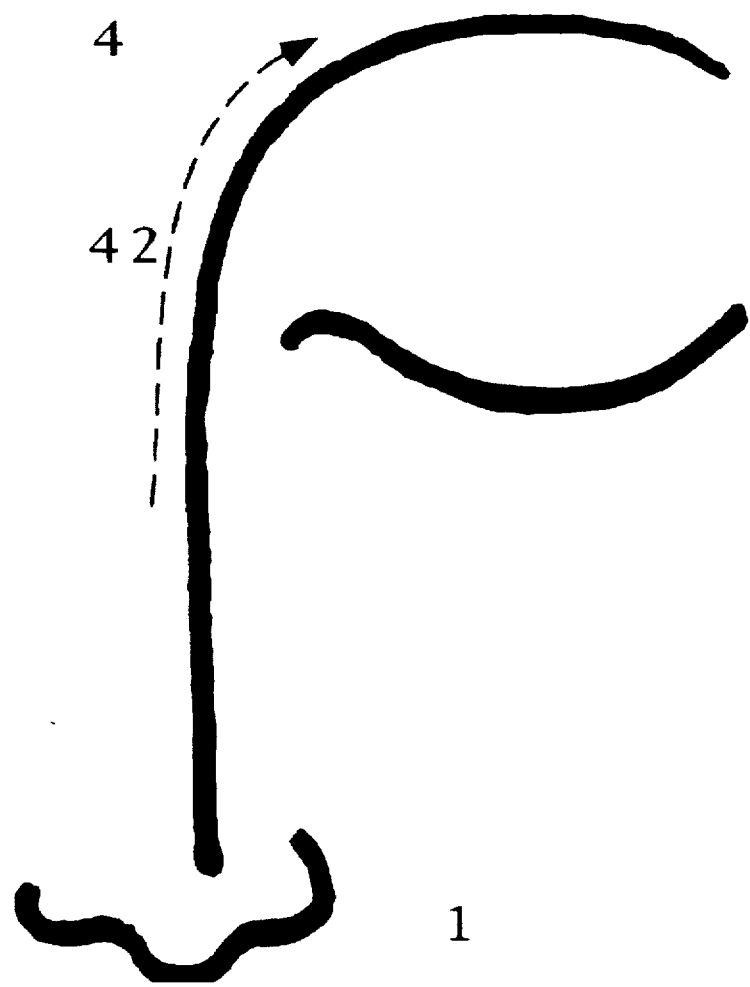
FIG. 5 is a schematic view of a portion of the face showing the fourth position of foundation application.

Optionally, referring to FIG. 5, a small amount of foundation can be used to place a dot between the eyes at fourth position 4. Thereafter, the finger containing the residue of the foundation is moved straight up between the eyes and just over the brows, as shown at 42. Care should be taken to avoid going more than ½ inch above the brows. The coverage in these areas ought to be very light. It has been found that most people do not need foundation above the brows, even though for many the skin is much lighter close to the brows. In such cases, foundation may be blended into the top of the brows somewhat if coverage is needed there, using care to avoid placement of foundation on any hairs of which the brows are comprised. During this step the user should make sure that foundation applied on the nose at first position 1 meets and blends with the foundation applied to fourth position 4.

Figure 6:
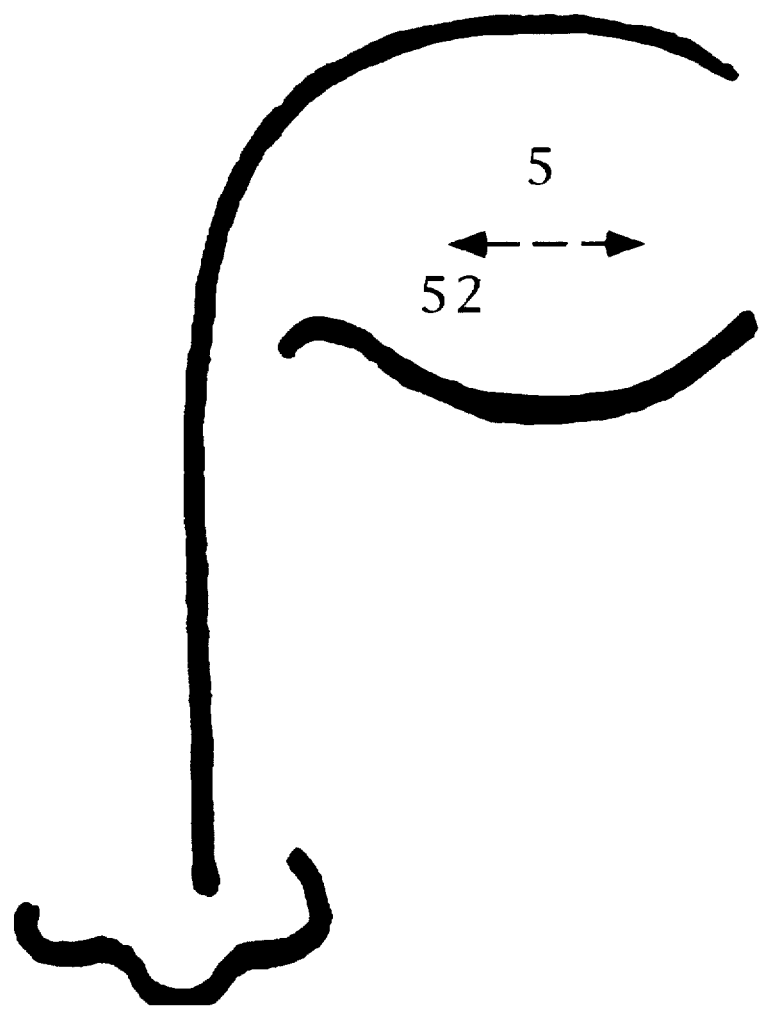
FIG. 6 is a schematic view of a portion of the face showing the fifth position of foundation application.

Optionally, referring to FIG. 6, foundation can be placed at fifth position 5. Blending of foundation at fifth position 5 occurs in an outward and upward direction. With what is left on the finger, proceed into the corner of the eyelid by the nose. Foundation may be applied to cover the eye from lash to brow if desired, or applied to cover the eyelid, solely.

Using a dry finger, the user then proceeds to touch a continuum of points along substantially the entire length of the outer boundary of the keyhole shaped, preselected area 10 to blend the foundation with the skin therealong and define the preselected area, causing the foundation to be imperceptible where it ends. During this step, foundation is applied by finger stroke in a direction which is preferably toward the center of the face, but can alternatively be outward toward the hairline.

Figure 7:
FIG. 7 is a schematic view of a portion of the face showing positions of application of blush to the cheekbone.

As shown in FIG. 7, blush is applied to the cheekbone with a brush or finger at a first position 1, located behind and below the eye, and stroking the brush toward the ear and temples. Next, but without adding additional blush to the brush or finger, blush is again applied, but now at a second position 2 and again stroked toward the ear. Lastly, with the product that is left, blush is applied at a third position 3 and again stroked toward the ear. Application in this manner ensures that the applied blush is darkest at position 1, medium at position 2, and lightest at position 3. The method for application of blush to the cheekbone as described hereinabove with reference to FIG. 7 can additionally be utilized to apply contour powder to the hollow of the cheek, in which event the first, second and third positions would be located immediately under the cheekbone. Further, the method for application of blush to the cheekbone as described with reference to FIG. 7 can be used to apply highlighter in the form of a lighter shade of powder or cream, or a frosted shade of powder or cream, to the top of the cheekbone a half inch above the bone as it rounds toward the eyes, in which event the first, second and third positions would be located immediately over the cheekbone.

Figure 8:
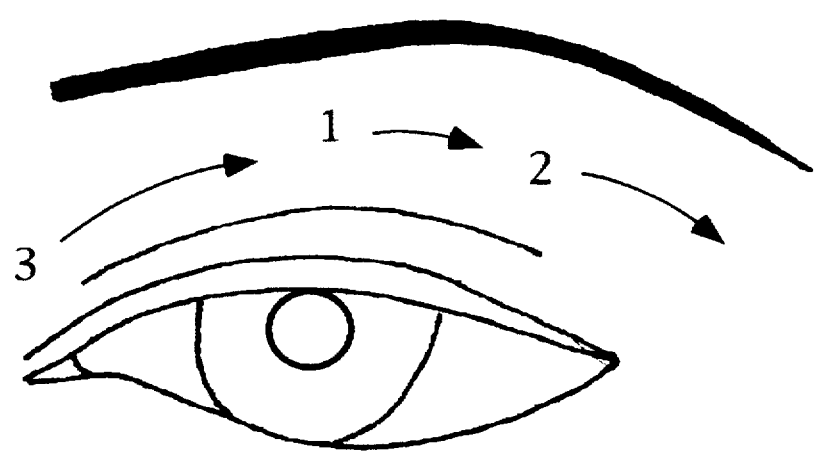
FIG. 8 is a schematic view of the left eye and the three positions of application of eye shadow.

As shown in FIG. 8, eye shadow is applied to the upper eye by placing eye shadow at a first position 1, and stroking the eye shadow toward the ear. The first position is located on the eyelid and/or along the contour area therebehind and above the center of the eye. Next, but without adding additional eye shadow to the applicator, place eye shadow at a second position 2, and stroke the eye shadow toward the ear. The second position 2 is located between the first position and the outer corner of the eye. Place eye shadow at a third position 3, and stroke the eye shadow toward the ear. The third position 3 is located between the first position and the inner corner of the eye. In this manner of application, eye shadow is darkest at the first position 1, medium at the second position 2, and lightest at position 3.

Figure 9:
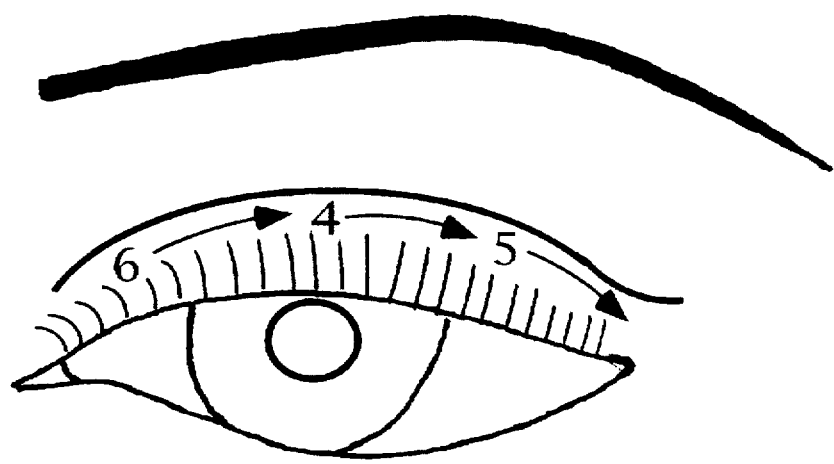
FIG. 9 is a schematic view of the left eye and the three positions of application of a second shade of eyeshadow.

Optionally, as shown in FIG. 8, the method for application of eye shadow, as described above, functions as a base or contour. As shown in FIG. 9, application of make-up to the eye is further enhanced by placing a different or second shade of eye shadow at a fourth position 4, and stroking it toward the outer corner of the eye. The fourth position is located at the outer edge of the eyelid and above the center of the eye. Next, the second shade of eye shadow is placed at a fifth position 5, and stroked toward the outer corner of the eye. The fifth position 5 is located on the eyelid between the fourth position 4 and the outer corner. Finally, the second shade of eye shadow is placed at a sixth position 6, and stroked toward the outer corner of the eye, while never adding more color to the applicator. The sixth position 6 is located on the eyelid between the fourth position 4 and the inner corner of the eye. In this manner of application, eye shadow is darkest at the fourth position 4, medium at the fifth position 5, and lightest at the sixth position 6.

Figure 10:
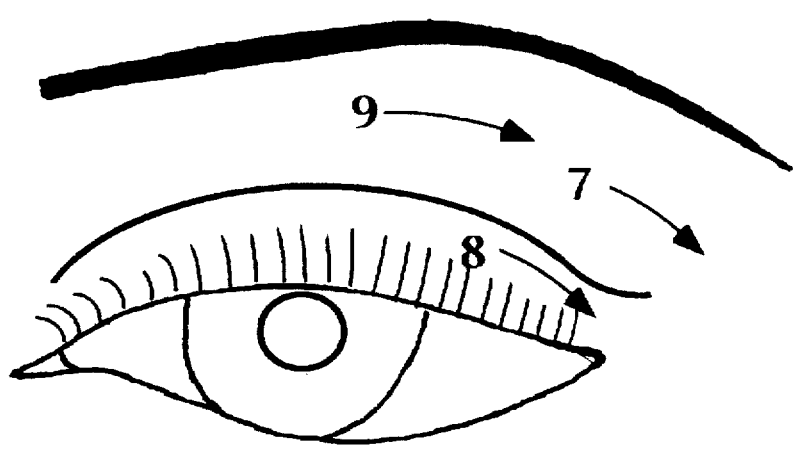
FIG. 10 is a schematic view of the left eye and the three alternative positions of application of a third shade of eyeshadow.

Alternatively, there is shown in FIG. 10, a method for application of a third shade of eye shadow, the method being accomplished by placing the third shade of eye shadow at a seventh position 7, and stroking it toward the outer corner of the eye. The seventh position 7 is located at the outer edge of the eyelid and between the center and the outer corner of the eye. Next, the third shade of eye shadow is placed at an eighth position 8, and stroked toward the outer corner of the eye. The eighth position 8 is located at the outer edge of the eyelid between the seventh position 7 and the outer corner of the eye. Finally, the third shade of eye shadow is placed at a ninth position 9, and stroked toward the outer corner of the eye. The ninth position 9 is located at the outer edge of the eyelid between the seventh position 7 and the center of the eye. In this manner the application of overlapping of singular eyeshadow to the eyelid is darkest at position 7, medium at position 8 and lightest at position 9.

Figure 11:
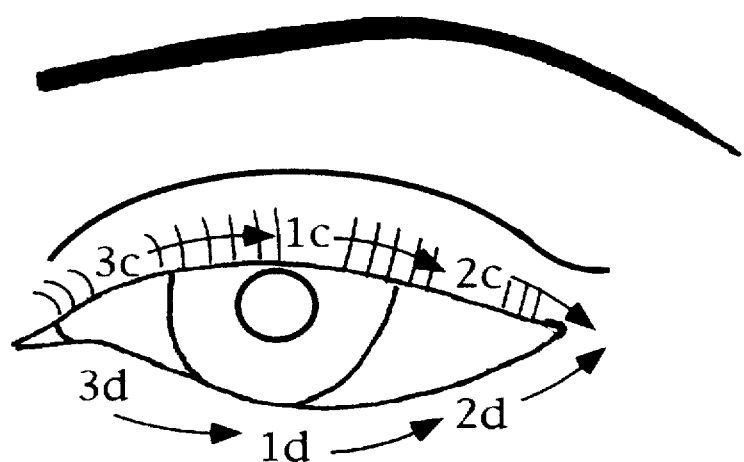
FIG. 11 is a schematic view of the left eye and the 1-2-3 method for application of additional shades of powder or eyeliner.

Additional shades of powder or eyeliner are added in a 1-2-3 pattern as shown in FIG. 11. Eyeliner is applied to the eyelid at a first position 1c toward a second position 2c and continuing toward the outer edge of the eye. Without adding more product, continue application from position 3c toward the outer edge of the eye to meet and blend at position 1c. Begin application of eyeliner just below the eye at first position 1d toward second position 2d and continuing toward the outer edge of the eye. Without adding more product, continue from third position 3d toward the outer edge of the eye to meet and blend at position 1d.

Having thus described the invention in rather full detail, it will be understood that such detail need not be strictly adhered to, but that additional variations and modifications may suggest themselves to one skilled in the art, all falling within the scope of the invention as defined by the subjoined claims.

What is claimed is:

1. A method for applying make-up to a preselected area of the face that is centered therewithin and encompasses the eyes, nose mouth and cheeks thereof, said method comprising the steps of:

a. placing a sizable first dot of foundation at a first position on each side of the nose near the nostrils;

b. stroking upward from said first position to meet the bridge of said nose;

c. blending foundation contained by said first dot to cover the entire front and sides of said nose, whereby said nostrils retain enough of said foundation to cover red skin thereabout;

d. placing a sizable second dot of said foundation on each side of said nose at a second position, said second position being under the corner of each eye immediately adjacent to said nose;

e. spreading the foundation contained by said second dot away from said nose while maintaining substantial coverage near said second position, thereby covering the skin very close to the lower eyelashes;

f. blending said foundation downward;

g. applying an additional quantum of said foundation in a back and forth motion at a third position, said third position being above and below the mouth, and including the bottom of said nose; and h. stroking said foundation from a continuum of points forming the outer boundary of said preselected area toward the center of the face, thereby blending said foundation into surrounding skin along substantially the entire length of said outer boundary to define said preselected area.

2. A method for applying make-up, as recited by claim 1, further comprising the steps of:

i. filling pores around the sides of said nostrils with moisturizer;

j. filling said pores around the sides of said nostril with said foundation; and, optionally, k. applying powder over the foundation which covers said pores.

3. A method for application of make-up, as recited by claim 1, further comprising the steps of:
   j. filling said pores around the sides of said nostril with said foundation; and
   k. applying powder over the foundation which covers said pores.

4. A method for application of make-up, as recited by claim 1 further comprising the step of filling said pores around the sides of said nostril with said foundation.

5. A method for application of make-up, as recited by claim 1 further, comprising the steps of:
   q. covering the lips with foundation to tone down the natural lip color thereof and prevent it from blending with and changing the shade of lipstick appointed for application; and
   r. applying lipstick to the lips.

6. A method for application of make-up, as recited by claim 1, further comprising the step of applying foundation along a continuum of points located at the outer edges of the lips to diminish the apparent shape or size thereof.

7. A method as recited by claim 6, wherein the shape of the lips is changed by application of lip liner or lipstick using a lip brush applicator comprising the steps of:
   (i) placing the applicator at a first position located at either side of the peaks of the upper lip and stroking toward position two along the outer edge of the upper lip so as to push the muscle line as far as possible without going onto the skin, position two being located between the peak of the upper lip and the outer corner of the mouth;
   (ii) stroke as in step one from position two to the outer corner of the mouth;
   (iii) place the applicator at position three located at the center of the peaks of the upper lip and stroke toward position one to meet and blend with each of the peaks;
   (iv) place the applicator at position one located immediately under the outer corner of the mouth and stroke downward toward position two, position two being located between the outer corner and the center of the lower lip;
   (v) stroke from position two to position three located at the center of the lip; and
   (vi) place the applicator at position three and stroke back to meet position 2 to finalize the lip line;
   (vii) repeating steps i through vi to finalize lip line on both sides of the mouth; and
   (viii) filling in the body of the lips with lipstick using a lipstick tube or lipstick brush applicator.

8. A method for application of make-up, as recited by claim 1, further comprising the steps of:
   l. placing said foundation at a fourth position, said fourth position being between the eyes;
   m. blending said foundation upward between the eyes to not more than ½ inch above the brows; and
   n. blending said foundation at the bridge of the nose into said foundation near said first position, whereby coverage of said foundation is light.

9. A method for application of make-up, as recited by claim 1 further comprising the steps of:
   o. placing said foundation at a fifth position, said fifth position being located in the center of the eyelids; and
   p. blending out and up, and into the corner of the eye near said nose.

10. A method for application of blush to the cheekbone, comprising the steps of:
    a. placing blush at a first position, and stroking said blush toward the ear and temple, said first position being located below the eye and between said eye and said ear;
    b. placing blush at a second position, and stroking said blush toward said ear, said second position being located between said first position and said ear and temple;
    c. placing blush at a third position, and stroking said blush toward said ear, said third position being located between said first position and said eye, whereby said blush is darkest at said first position, medium at said second position and lightest at said third position and wherein said blush is contour powder, said contour powder is applied to the hollow of the cheek and said first, second, and third positions are located immediately under the cheekbone.

11. A method for application of make-up under an eye having the steps of:
    a. placing foundation on a finger tip or applicator;
    b. applying said foundation at a first position;
    c. stroking said foundation toward a second position;
    d. applying said foundation at a third position, said third position being directly under and into the lashes; and
    e. stroking said foundation toward the nose.

12. A method for application of make-up under an eye having the steps of:
    a. placing concealer on a finger tip;
    b. applying said concealer at a first position;
    c. stroking said concealer toward a second position;
    d. stroking said concealer toward a third position, so that said concealer goes slightly into the lashes;
    e. placing foundation on a finger tip;
    f. patting said foundation at a first position over said concealer;
    g. replenishing said foundation and patting it over said concealer to said second position;
    h. applying said foundation by patting at a third position, said third position being directly under and into the lashes; and
    i. patting said foundation toward or away from the nose.

13. A method for application of highlighter to enhance bone structure, comprising the steps of:
    a. placing highlighter at a first position, and stroking said highlighter toward the ear and temple, said first position being located below the eye and between said eye and said ear;
    b. placing highlighter at a second position, and stroking said highlighter toward said ear, said second position being located between said first position and said ear and temple;
    c. placing highlighter at a third position, and stroking said highlighter toward said ear, said third position being located between said first position and said eye, whereby said highlighter is in the form of a cream, or a frosted shade of powder or cream, and is darkest at said first position, medium at said second position and lightest at said third position, said highlighter being applied to the top of the cheek bone a half inch above the bone as it rounds toward the eyes, and whereby said first, second and third positions are located immediately over the cheekbone.

14. A method for application of eye liner comprising the steps of:
   a. placing an applicator containing a shade of eye liner or powder functioning as eye liner at a first position and stroking said shade of eye liner toward the outer corner of said eye, said first position being located at the outer edge of said eyelid above said center of said eye;
   b. placing said applicator at a second position, and stroking said eye liner toward said outer corner of said eye and down slightly into the eye lashes, said second position being located at said outer edge of said eyelid between said first position and said outer corner of said eye; and
   c. placing said applicator at a third position, and stroking said eye liner toward said outer corner of said eye, said third position being located at said outer edge of said eyelid between said first position and said inner corner of said eye.

* * * * *